(12) United States Patent
Vonthron et al.

(10) Patent No.: US 11,495,136 B1
(45) Date of Patent: Nov. 8, 2022

(54) SYSTEMS AND METHODS FOR ANALYZING AND TREATING LEARNING DISORDERS

(71) Applicant: bMotion Technologies, SAS, Palaiseau (FR)

(72) Inventors: Francois Vonthron, Paris (FR);
Antoine Yuen, Vitry sur Seine (FR);
Didier Bazoge, Champagne sur Seine (FR); Sebastien Desarmaux, Alfortville (FR)

(73) Assignee: bMotion Technologies, SAS, Palaiseau (FR)

( * ) Notice: Subject to any disclaimer, the term of this patent is extended or adjusted under 35 U.S.C. 154(b) by 0 days.

(21) Appl. No.: 17/456,312

(22) Filed: Nov. 23, 2021

(30) Foreign Application Priority Data

Sep. 21, 2021 (EP) .................................... 21315165

(51) Int. Cl.
*G09B 5/06* (2006.01)
*G10H 1/00* (2006.01)
(Continued)

(52) U.S. Cl.
CPC ............. *G09B 5/065* (2013.01); *G06V 20/40* (2022.01); *G06V 40/20* (2022.01); *G10H 1/0008* (2013.01);
(Continued)

(58) Field of Classification Search
CPC .......... G09B 5/06; G09B 5/065; G16H 20/70; G06V 20/40; G06V 40/20; G10H 1/00;
(Continued)

(56) References Cited

U.S. PATENT DOCUMENTS 8,907,193 B2 * 12/2014 Cross ....................... G10H 1/38
84/613
2012/0090446 A1 4/2012 Moreno
(Continued)

FOREIGN PATENT DOCUMENTS

WO WO-2016145372 A1 9/2016

OTHER PUBLICATIONS

Bieleninik et al., "Effects of Improvisational Music Therapy vs. Enhanced Standard Care on Symptom Severity Among Children With Autism Spectrum Disorder: The TIME—A Randomized Clinical Trial," JAMA, 318(6):525-535 (Aug. 2017).
(Continued)

*Primary Examiner* — Timothy A Musselman
(74) *Attorney, Agent, or Firm* — Eversheds Sutherland (US) LLP; Christopher C. Bolten; Joshua W. Branson

(57) ABSTRACT

Devices, systems, and methods are provided for analyzing and treating learning disorders using software as a medical device. A method may include identifying, by a device, application-based cognitive musical training (CMT) exercises associated with performance of software; receiving a first user input to generate a first sequence of the application-based CMT exercises; presenting a first application-based CMT exercise of the application-based CMT exercises based on the first sequence; receiving, during the presentation of the first application-based CMT exercise, a second user input indicative of a user interaction with the first application-based CMT exercise; generating, based on a comparison of the second user input to a performance threshold, a second sequence of the application-based CMT exercises, the first sequence different than the second sequence; and presenting a second application-based CMT exercise of the application-based CMT exercises based on the second sequence.

30 Claims, 6 Drawing Sheets

(51) Int. Cl.
 G16H 20/70 (2018.01)
 G06V 40/20 (2022.01)
 G06V 20/40 (2022.01)
(52) U.S. Cl.
 CPC ....... *G16H 20/70* (2018.01); *G10H 2210/071* (2013.01); *G10H 2210/091* (2013.01)
(58) Field of Classification Search
 CPC ............. G10H 1/0008; G10H 2210/07; G10H 2210/071; G10H 2210/09; G10H 2210/091
 See application file for complete search history.

(56) References Cited

U.S. PATENT DOCUMENTS

2016/0155354 A1  6/2016  Merzenich et al.
2017/0046971 A1  2/2017  Moreno

OTHER PUBLICATIONS

Bilhartz et al., "The Effect of Early Music Training on Child Cognitive Development," Journal of Applied Developmental Psychology, 20(4):615-636 (Dec. 1999).

Carlier et al., "Empowering Children with ASD and Their Parents: Design of a Serious Game for Anxiety and Stress Reduction," Sensors, 20(4):966 (Jan. 2020).

Dalton, C., Interaction Design in the Built Environment: Designing for the 'Universal User', Universal Design 2016: Learning From the Past, Designing for the Future, pp. 314-323. IOS Press. (2016).

Habibi et al., Music training and child development: a review of recent findings from a longitudinal study, Annals of the New York Academy of Sciences, 1423(1):73-81 (Jul. 2018).

Horowitz-Kraus, T., "The Role of Executive Functions in the Reading Process," Reading Fluency, pp. 51-63, Springer, Cham. (2016).

Jacquier-Roux, et al., "BALE: Batterie Analytique du Langage écrit," Groupe Cogni-Sciences, Laboratoire de Psychologie et NeuroCognition (2010).

Lonergan et al., "A meta-analysis of executive functioning in dyslexia with consideration of the impact of comorbid ADHD," Journal of Cognitive Psychology, 31(7):725-749 (Oct. 2019).

Powell et al., "Guideline Development for Technological Interventions for Children and Young People to Self-Manage Attention Deficit Hyperactivity Disorder: Realist Evaluation," Journal of Medical Internet Research, 21(4): e12831 (Apr. 2019).

Sanders, E. B., "From User-Centered to Participatory Design Approaches," Design and the Social Sciences, pp. 18-25, CRC Press (Apr. 2002).

Tang et al., "Designing a serious game for youth with ASD: Perspectives from end-users and professionals," Journal of Autism and Developmental Disorders, 49(3):978-995 (Mar. 2019).

Valentine et al., "A systematic review evaluating the implementation of technologies to assess, monitor and treat neurodevelopmental disorders: A map of the current evidence," Clinical Psychology Review, 80:101870 (Aug. 2020).

Yusoff et al., "Validation of Serious Games Attributes Using the Technology Acceptance Model," 2010 Second International Conference on Games and Virtual Worlds for Serious Applications, IEEE, pp. 45-51 (Mar. 2010).

Extended European Search Report dated Mar. 7, 2022 in EP Patent Application Serial No. 21315165.7.

* cited by examiner

SYSTEMS AND METHODS FOR ANALYZING AND TREATING LEARNING DISORDERS

CROSS-REFERENCE TO RELATED APPLICATION

This application claims priority to European Patent Application No. 21315165.7, filed Sep. 21, 2021, the entire contents of which are incorporated herein by reference.

TECHNICAL FIELD

This disclosure generally relates to devices, systems, and methods for analyzing and treating learning disorders.

BACKGROUND

Many people, including children, have neurodevelopmental disorders and lack access to care. Treatment of some learning disorders often involves the physical presence of a professional to treat a person with a learning disorder. Digital therapeutics as a replacement for the physical presence of a treatment professional are lacking.

Figure 1:
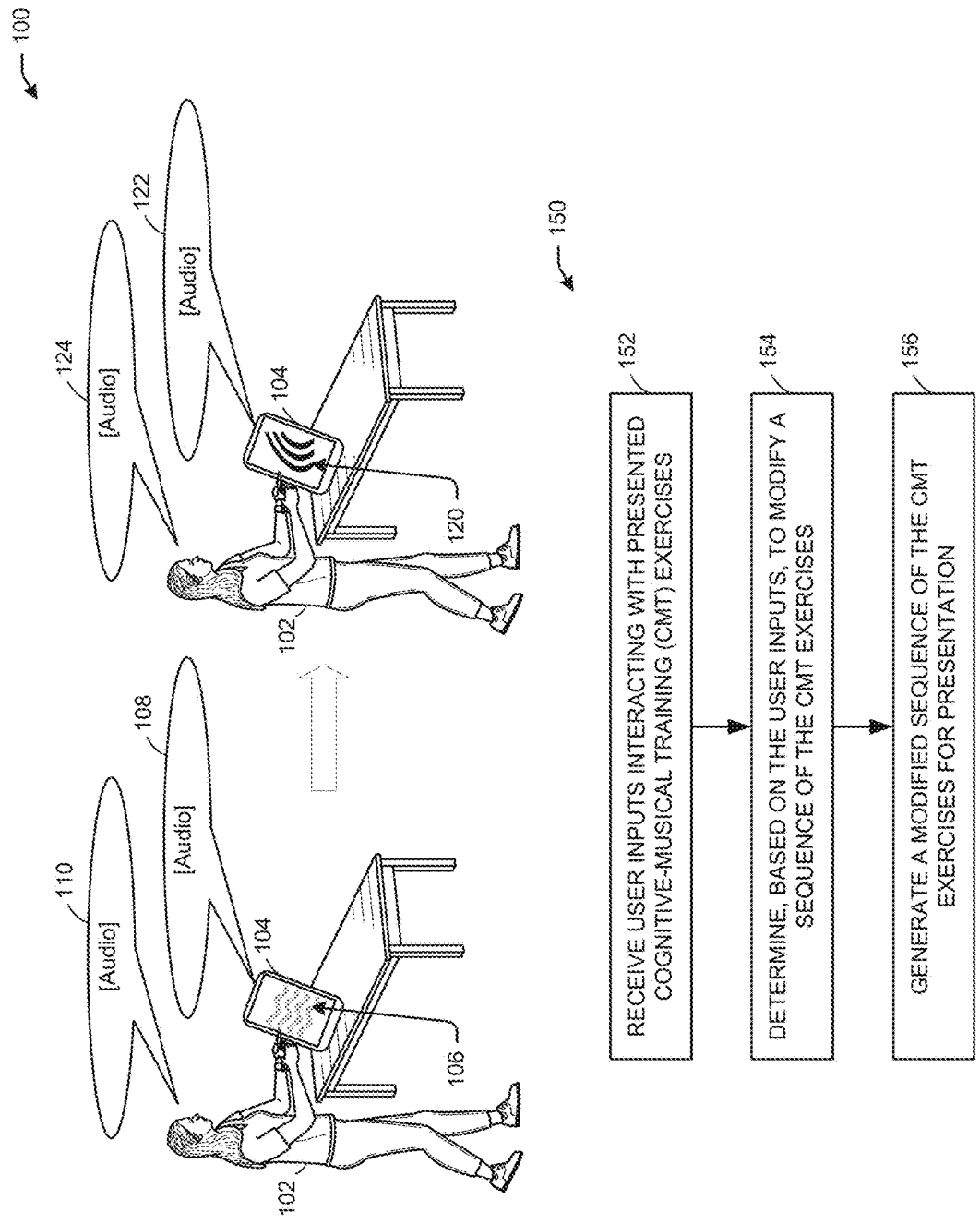
FIG. 1 illustrates an example environment for analyzing and treating learning disorders, in accordance with one or more example embodiments of the present disclosure.

Certain implementations will now be described more fully below with reference to the accompanying drawings, in which various implementations and/or aspects are shown. However, various aspects may be implemented in many different forms and should not be construed as limited to the implementations set forth herein; rather, these implementations are provided so that this disclosure will be thorough and complete, and will fully convey the scope of the disclosure to those skilled in the art. Like numbers in the figures refer to like elements throughout. Hence, if a feature is used across several drawings, the number used to identify the feature in the drawing where the feature first appeared will be used in later drawings.

DETAILED DESCRIPTION

Access to care for children with neurodevelopmental disorders (NDD) often is limited. Inequalities remain, notably due to significant disparities according to social background and place of residence. For example, in some geographic areas, children have less access to care, even though they are more likely to develop NDD. Improving the long-term follow-up of children is a healthcare objective, as care is too often interrupted after the first phases of rehabilitation, as for example in the case of Special Learning Disorders (SLDs). In addition, health-related isolation measures have increased the importance of developing training methods that can be used autonomously by the child. Without denying the disparities in use depending on the environment, a large majority of households are now equipped with at least one tablet, smartphone, or computer, including among the less developed areas.

Technology offers new possibilities to innovate in terms of care and to vary training methods because it allows the development of remote training protocols, for example via digital tools that can be accessed at low cost. Although the use of digital therapeutics is a promising solution, some existing systems and techniques do not provide software as a medical device (SaMD) that allows for learning and development without the physical presence of a health professional.

In particular, SaMD includes software intended for use of one or more medical purposes without medical device hardware. For example, SaMD used for the treatment of SLDs may not require a physical medical device to provide treatment to a patient. An example treatment for patients with SLDs is cognitive-musical training (CMT). However, CMT has not yet been developed as a SaMD, allowing for treatment of patients with SLDs without requiring a medical professional to be present.

There is therefore a need for enhanced systems and methods of analyzing and treating learning disorders.

In one or more embodiments, CMT exercises may be implemented as a SaMD. The CMT exercises may include a combination of interactive video and audio content. Different CMT exercises may present different challenges that test and develop cognitive abilities by providing visual and auditory cues to which a user (e.g., patient) may respond using words, gestures, touches (e.g., of screens, buttons, etc.), and the like. When a user input represents a request to generate and present the exercises (e.g., opening the application, selecting "start," etc.), a first device may generate a sequence of available CMT exercises in some order. The CMT exercises may be maintained remotely on another device, updated, and provided to the first device, allowing the first device to present the CMT exercises stored on the first device without needing to connect to the other device. In this manner, the CMT exercises may be part of downloadable SaMD using a CMT computer program executable by the first device. In particular, the software program may be a SaMD native application that is downloadable onto the first device.

In one or more embodiments, as a user responds to the presented visual and/or audio cues of a CMT exercise presented using the first device, the first device may determine if the user's responses correspond to the cues (e.g., by touching, moving, gesturing, or speaking based on the cues and/or within a time limit from a presented cue). The first device may generate a score based on the user's responses, the scoring indicating whether the user's responses met performance thresholds (e.g., the user's responses were the proper responses provided within threshold amounts of time). When the score exceeds a score threshold, such may indicate that the user completed the CMT exercise properly, and the next CMT exercise in the sequence of exercises may commence, repeating the interaction and evaluation processes. When the user's score is too low (e.g., the user did not respond to the cues and/or did not respond quickly enough), such may indicate that the user struggled to complete the CMT exercise properly. As a result, the first device may revise the sequence of CMT exercises by generating a different CMT exercise sequence for presentation.

In one or more embodiments, the CMT exercises may be based on the following principles: (1) Music-language analogies: training dyslexics with rhythmic auditory cues could contribute to improve brain circuits which are common to music and language processes. (2) The temporal and rhythmic features of music, which could exert a positive effect on the multiple dimensions of the "temporal deficit" characteristic of some types of dyslexia. (3) Cross-modal integration, based on converging evidence of impaired connectivity between brain regions in dyslexia and related disorders. The CMT exercises may act as a therapeutic rehabilitation program for SLDs.

In one or more embodiments, the CMT exercises may include both rhythmic and musical tasks and exercises based on the following components and active listening to musical stimuli: (1) An auditory component targeting the language-music similarity in auditory perception. (2) A motor component, mainly focusing on rhythm production and imitation. (3) A cross-modal component, making special demands on simultaneous processing of information from different modalities including auditory, visual, sensory, and motor modalities as well as their combinations. In this manner, the first device may include a visual display, an audio output (e.g., speakers), microphones, cameras, motion sensors (e.g., accelerometers), touch sensors (e.g., haptic sensors), and the like to present the CMT exercises and detect the user's responses/interactions.

In one or more embodiments, the SaMD may be used autonomously by children aged 7-11 who meet the Diagnostic and Statistical Manual of Mental Disorders (DSM-V) criteria for SLD or who respond to the DSM-V criteria for SLD according to a health professional or regulatory agency.

In one or more embodiments, the CMT exercises may represent varying degrees of difficulty for the user to complete. For example, some CMT exercises may have longer sequences than others and therefore may be more difficult to complete. Some CMT exercises may require shorter response times to visual and audible cues than other CMT exercises. A more difficult CMT exercise may include visual disruptors that hide a character's and player's rhythmic sequences, pushing the player to use more of their acquired rhythmic skills. A sequence of CMT exercises may be organized in a manner in which the CMT exercises increase in difficulty, allowing a user to begin with an easier CMT exercise, and progress to more difficult CMT exercises. The CMT exercises may include an introduction (e.g., contextualizing the game at its launch), instructions regarding how the game works (e.g., a user manual), an image and text sequence to describe a particular CMT exercise, rhythmic sequences, visual and auditory cues, audio and visual feedback, use of special effects, description of graphic assets, animation, a presentation of an "end" screen and user score, and the like. One or more CMT exercises may be part of a larger storyline so that completion of the CMT exercise tasks (e.g., user responses to the cues) allows for progression of the storyline.

In one or more embodiments, the CMT exercises may include multiple tasks for which a user is cued. One task may be to "follow" a leader by tapping or otherwise touching a device (e.g., a touchscreen), such as by swiping. The tapping could be anywhere on a device, or may require a specific portion of the screen (e.g., left side vs. right side, etc.). Another task may be to clap hands according to a beat/rhythm. Another task may be to shake or otherwise move a device (e.g., according to a beat/rhythm). Another task may be to sing or provide other verbal responses according to a beat/rhythm. Another task may be to tap or otherwise touch a device in accordance with a beat/rhythm. Another task may include a motion (e.g., punching, waving, etc.) in accordance with a beat/rhythm. Another task may include a user selection of words or other objects (e.g., based on tapping, touching, etc.). User motion and gestures may be detected by a device camera (e.g., image data of the user may be analyzed to determine whether a movement was executed within a limited time period). Device motion may be detected by an accelerometer to determine whether a user moved a device within a limited time period. Audio responses (e.g., singing, talking) of a user may be detected by a microphone and analyzed to determine that an audio response in general, or specific (e.g., using audio processing and natural language processing to identify keywords), was communicated within a limited time period. Device touching may be measured by pressure sensors (e.g., haptic sensors) that detect contact pressure (e.g., with a touchscreen), and may be compared to a time threshold. The time periods/thresholds used to measure whether a user's interaction occurred quickly enough to satisfy rules of a CMT exercise may be considered performance thresholds. The performance thresholds may represent amounts of time before or after a beat and during which the user is required to respond according to a cue (e.g., a beat of a song, a graphic displayed, etc.). The performance thresholds also may include the length of a user action (e.g., how long the user held a note when singing) or the percentage of task completion (e.g., a percentage of a song that the user actually sings in comparison to an entire song).

In one or more embodiments, scoring player's performance SP may be based on rhythmic synchronization through multiple modalities of interaction (sometimes combined). Player's responses are captured through accelerometers, microphones, cameras, and pressure sensitive screens. By assessing the audio-motor synchronization of the child with the rhythmic instruction, a device may define (i) a time T which corresponds to the exact moment when the player's input is expected (whatever the interaction mode); (ii) tolerance thresholds as in a Likert scale: tPerfect<tGood<tCorrect. The different intervals allow the device to assess the quality of the user's response with four levels of acceptance. An input may be considered accepted when it is in the interval [T−tCorrect; T+tCorrect] and refused otherwise. An input of better quality, either in the interval [T−tGood; T+tGood] or in the interval [T−tPerfect; T+tPerfect], may result in a different visual and audio feedback to the child. In one version, a simplified score calculation may account for the ratio of accepted user inputs to total inputs. When a user's score exceeds a score threshold, the user has completed the CMT exercise and may progress to another (e.g., more difficult) exercise. When the user's score is below the score threshold, the user may be presented with the same CMT exercise, or another CMT exercise of similar or less difficulty.

In one or more embodiments, the remote devices that store, generate, update, and provide CMT exercises to client devices may exercise data security in accordance with relevant laws and regulations, and with user consent. For example, the remote devices may operate consistent with General Data Protection Regulation (GDPR), limiting access to the data, and implementing an additional layer of rights management at a database level to partition access to user data. For example, when a user connects to the application, the remote devices may generate a token to allow the user to access only the user's data even if the user attempted to call application programming interfaces (APIs) directly to request data of other users.

The above descriptions are for purposes of illustration and are not meant to be limiting. Numerous other examples, configurations, processes, etc., may exist, some of which are described in greater detail below. Example embodiments will now be described with reference to the accompanying figures.

FIG. 1 illustrates an example environment for analyzing and treating learning disorders, in accordance with one or more example embodiments of the present disclosure.

Figure 3:
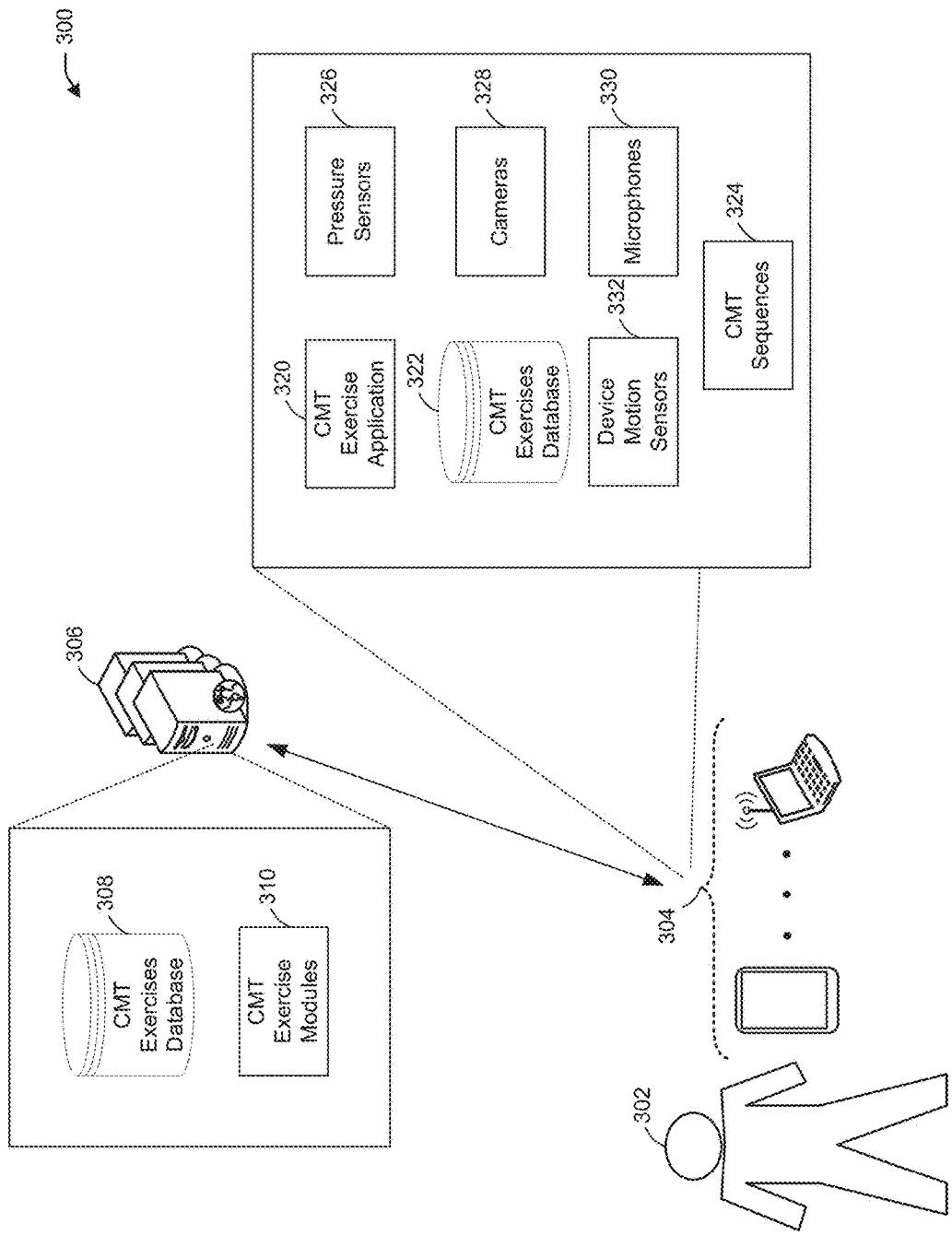
FIG. 3 depicts an example system for analyzing and treating learning disorders, in accordance with one or more example embodiments of the present disclosure.

Referring to FIG. 1, a user 102 (e.g., a patient) may interact with software using a device 104 (e.g., the software functioning as a SaMD) that presents CMT exercises for therapy for the user 102. The CMT exercises may include video 106 and audio 108 (e.g., instructions, songs, cues, etc.). The user 102 may be prompted to interact with the video 106 and/or the audio 108 by touching, tapping, swiping, gesturing, moving the device 104 (e.g., rotating), clapping, and/or communicating verbally (e.g., singing, speaking etc., represented by audio 110 as shown). As part of a process 150, the user interactions may be captured by the device 104 (e.g., using microphones, cameras, or other sensors as shown in FIG. 3) and analyzed by the device 104 to determine whether the user 102 provided the correct interactions as user inputs, within time thresholds (e.g., before or after a visual or rhythmic cue), and/or for a time duration.

Still referring to FIG. 1, the process 150 may, at block 152, receive the user inputs that represent user interactions with the CMT exercises presented by the device 104. At block 154, the device 104 may determine, based on the user inputs, to modify a sequence of the CMT exercises (e.g., the order in which the CMT exercises are presented) based on whether the user inputs indicate a successful user completion of the CMT exercises according to performance criteria. At block 156, the device 104 may generate a modified sequence of the CMT exercises for further presentation. The modified sequence may be a re-ordering of the CMT exercises stored by the device 104, and/or may include additional/modified CMT exercises provided to the device 104 (e.g., as explained with respect to FIG. 3).

Still referring to FIG. 1, the modified sequence of the CMT exercises may be presented to the user 102 using the device 104. For example, another CMT exercise may be presented using video 120 and audio 122 (e.g., instructions, songs, cues, etc.). The user 102 may be prompted to interact with the video 106 and/or the audio 108 by touching, tapping, swiping, gesturing, moving the device 104 (e.g., rotating), clapping, and/or communicating verbally (e.g., singing, speaking etc., represented by audio 124 as shown). The process 150 may be repeated to analyze whether the user's interactions with the CMT exercise satisfied the performance criteria of the CMT exercise, and whether the sequence of CMT exercises again needs modification.

In one or more embodiments, as the user 102 responds to the presented video 106 and/or audio 108 cues of a CMT exercise presented using the device 104, the device 104 may determine at block 154 if the user's responses correspond to the cues (e.g., by touching, moving, gesturing, or speaking based on the cues and/or within a time limit from a presented cue). The device 104 may generate a score based on the user's responses, the scoring indicating whether the user's responses met performance thresholds (e.g., the user's responses were the proper responses provided within threshold amounts of time). When the score exceeds a score threshold, such may indicate that the user completed the CMT exercise properly, and the next CMT exercise in the sequence of exercises may commence, repeating the interaction and evaluation processes. When the user's score is too low (e.g., the user did not respond to the cues and/or did not respond quickly enough), such may indicate that the user struggled to complete the CMT exercise properly. As a result, the device 104 may revise, at block 156, the sequence of CMT exercises by generating a different CMT exercise sequence for presentation.

In one or more embodiments, the CMT exercises may include both rhythmic and musical tasks and exercises based on the following components and active listening to musical stimuli: (1) An auditory component targeting the language-music similarity in auditory perception. (2) A motor component, mainly focusing on rhythm production and imitation. (3) A cross-modal component, making special demands on simultaneous processing of information from different modalities including auditory, visual, sensory, and motor modalities as well as their combinations. In this manner, the first device may include a visual display, an audio output (e.g., speakers), microphones, cameras, motion sensors (e.g., accelerometers), touch sensors (e.g., haptic sensors), and the like to present the CMT exercises and detect the user's responses/interactions.

In one or more embodiments, the CMT exercises may represent varying degrees of difficulty for the user to complete. For example, some CMT exercises may have longer sequences than others and therefore may be more difficult to complete. Some CMT exercises may require shorter response times to visual and audible cues than other CMT exercises. A more difficult CMT exercise may include visual disruptors that hide a character's and player's rhythmic sequences, pushing the player to use more of their acquired rhythmic skills. A sequence of CMT exercises may be organized in a manner in which the CMT exercises increase in difficulty, allowing the user 102 to begin with an easier CMT exercise, and progress to more difficult CMT exercises. The CMT exercises may include an introduction (e.g., contextualizing the game at its launch), instructions regarding how the game works (e.g., a user manual), an image and text sequence to describe a particular CMT exercise, rhythmic sequences, visual and auditory cues, audio and visual feedback, use of special effects, description of graphic assets, animation, a presentation of an "end" screen and user score, and the like. One or more CMT exercises may be part of a larger storyline so that completion of the CMT exercise tasks (e.g., user' responses to the cues) allows for progression of the storyline.

In one or more embodiments, the CMT exercises may include multiple tasks for which the user 102 is cued. One task may be to "follow" a leader by tapping or otherwise touching a device (e.g., a touchscreen), such as by swiping. The tapping could be anywhere on a device, or may require a specific portion of the screen (e.g., left side vs. right side, etc.). Another task may be to clap hands according to a beat/rhythm. Another task may be to shake or otherwise move a device (e.g., according to a beat/rhythm). Another task may be to sing or provide other verbal responses according to a beat/rhythm. Another task may be to tap or otherwise touch a device in accordance with a beat/rhythm. Another task may include a motion (e.g., punching, waving, etc.) in accordance with a beat/rhythm. Another task may include a user selection of words or other objects (e.g., based on tapping, touching, etc.). The time periods/thresholds used to measure whether a user's interaction occurred quickly enough to satisfy rules of a CMT exercise (e.g., block 154) may be considered performance thresholds. The performance thresholds may represent amounts of time before or after a beat and during which the user 102 is required to respond according to a cue (e.g., a beat of a song, a graphic displayed, etc.). The performance thresholds also may include the length of a user action (e.g., how long the user held a note when singing) or the percentage of task completion (e.g., a percentage of a song that the user 102 actually sings in comparison to an entire song).

In one or more embodiments, scoring player's performance SP may be based on rhythmic synchronization through multiple modalities of interaction (sometimes combined). Player's responses are captured through accelerometers, microphones, cameras, and pressure sensitive screens. By assessing the audio-motor synchronization of the child with the rhythmic instruction, a device may define (i) a time T which corresponds to the exact moment when the player's input is expected (whatever the interaction mode); (ii) tolerance thresholds as in a Likert scale: tPerfect<tGood<tCorrect. The different intervals allow the device to assess the quality of the user's response with four levels of acceptance. An input may be considered accepted when it is in the interval [T−tCorrect; T+tCorrect] and refused otherwise. An input of better quality, either in the interval [T−tGood; T+tGood] or in the interval [T−tPerfect; T+tPerfect], may result in a different visual and audio feedback to the child. In one version, a simplified score calculation may account for the ratio of accepted user inputs to total inputs. When a user's score exceeds a score threshold, the user has completed the CMT exercise and may progress to another (e.g., more difficult) exercise. When the user's score is below the score threshold, the user may be presented with the same CMT exercise, or another CMT exercise of similar or less difficulty (e.g., block 156).

Figure 2:
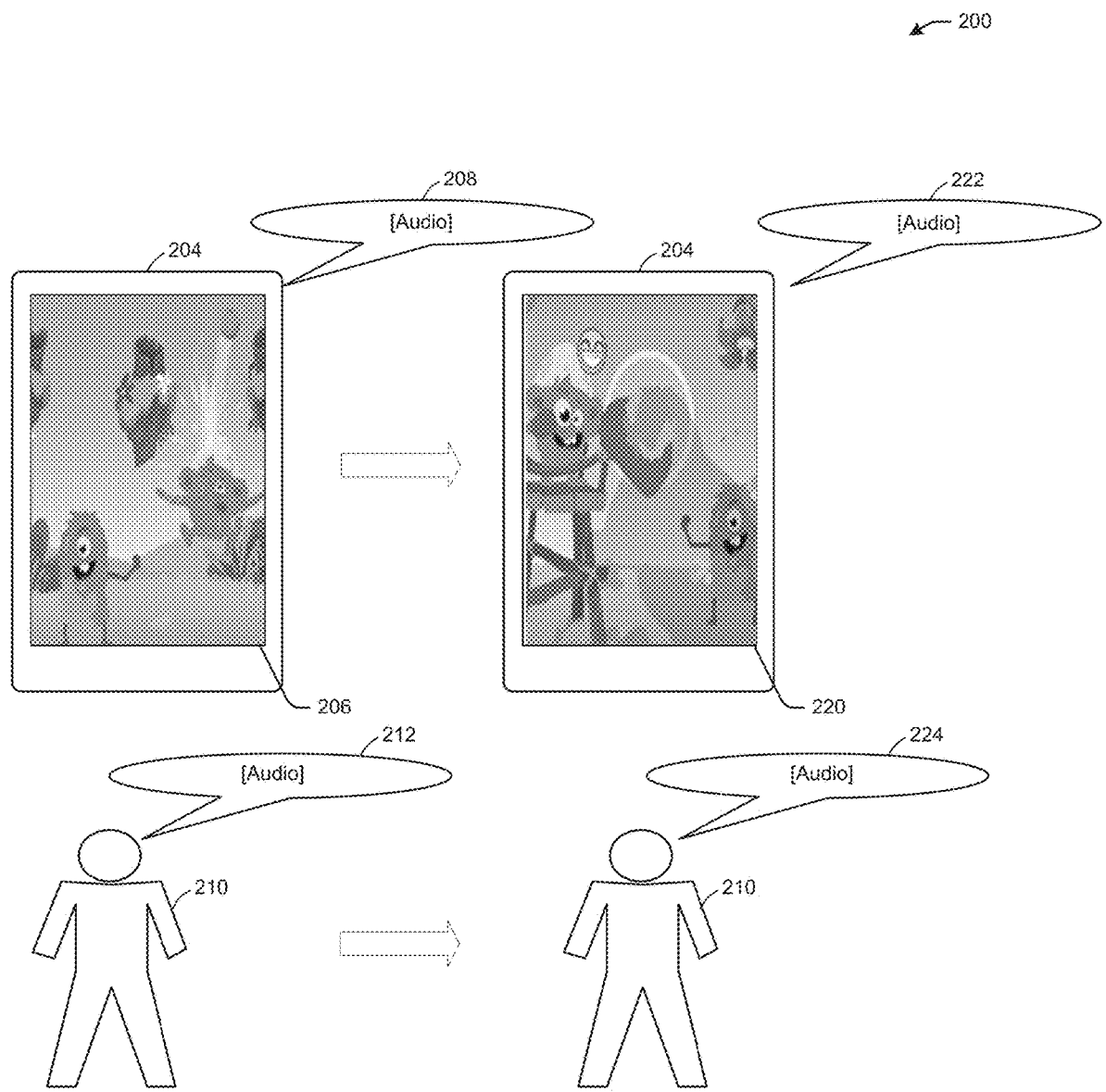
FIG. 2 illustrates example presentations of content for use in analyzing and treating learning disorders, in accordance with one or more example embodiments of the present disclosure.

FIG. 2 illustrates example presentations 200 of content for use in analyzing and treating learning disorders, in accordance with one or more example embodiments of the present disclosure.

Referring to FIG. 2, a device 204 (e.g., similar to the device 104 of FIG. 1) may present CMT exercises that include video 206 (e.g., graphics, images, text, etc., including characters controlled by a player, other characters, etc.) and audio 208, which may include a rhythm/beat to which a user 210 may be instructed to respond with motions, gestures, touches, speech/singing (e.g., audio 212), and the like. The user 210 may provide additional inputs (e.g., audio 224) based on the visual and/or audio cues represented by the video 220 and/or the audio 222 (e.g., the video 220 and/or the audio 222 may represent different exercises than the video 206 and/or the audio 208, and may be selected based on the user inputs to the video 206 and/or the audio 208). Depending on whether the user's responses as inputs to the CMT exercise, the device 204 may present additional video 220 and audio 222 of another CMT exercise, either as a progression of a CMT exercise, a subsequent CMT exercise in a sequence of CMT exercises, or a modified sequence of CMT exercises (e.g., block 156 of FIG. 1).

FIG. 3 depicts an example system 300 for analyzing and treating learning disorders, in accordance with one or more example embodiments of the present disclosure.

Referring to FIG. 3, the system 300 may include a user 302 of devices 304 (e.g., the device 104 of FIG. 1, the device 204 of FIG. 2, etc.), which may communicate with one or more remote devices 306 (e.g., servers, cloud-based devices, etc.). The one or more remote devices 306 may include a database of CMT exercises 308 that stores CMT exercises presentable using the devices 304, and CMT exercise modules 310 for generating CMT exercises presentable using the devices 304. The devices 304 may access the CMT exercises locally using an executable CMT exercise application 320, allowing the devices 304 to access the CMT exercises even when disconnected from the one or more remote devices 306.

Still referring to FIG. 3, the devices 304 may include the executable CMT exercise application 320 that may operate using the devices 304 for the purpose of SaMD treatment of the user 302. The devices 304 may include a database 322 of CMT exercises provided by the one or more remote devices 306. The devices 304 may generate CMT exercise sequences 324 representing sequential orders of the CMT exercises stored in the CMT exercise database 322. The devices 304 may include pressure sensors 326 for detecting user touches of the devices 304. The devices 304 may include cameras 328 for capturing images of the user 302 (with user consent and in accordance with relevant regulations), and microphones 330 for capturing audio of the user 302 (with user consent and in accordance with relevant regulations). The devices 304 may include device motion sensors 332 (e.g., accelerometers, magnetometers, etc.) for detecting device motion (e.g., device rotations, etc.).

In one or more embodiments, CMT exercises may be implemented as a SaMD. The CMT exercises may include a combination of interactive video and audio content. Different CMT exercises may present different challenges that test and develop cognitive abilities by providing visual and auditory cues to which the user 302 (e.g., patient) may respond using words, gestures, touches (e.g., of screens, buttons, etc.), and the like. When a user input represents a request to generate and present the exercises (e.g., opening the CMT exercise application 320), a first device of the devices 304 may generate a sequence of available CMT exercises in some order (e.g., one of the CMT exercise sequences 324). The CMT exercises may be maintained remotely at the one or more remote devices 306, updated, and provided to the first device, allowing the first device to present the CMT exercises stored on the first device without needing to connect to the one or more remote devices 306. In this manner, the CMT exercises may be part of downloadable SaMD using a the CMT exercise application 320 executable by the first device. In particular, the CMT exercise application 320 may be a SaMD native application that is downloadable onto the first device.

In one or more embodiments, as the user 302 responds to the presented visual and/or audio cues of a CMT exercise presented using the first device (e.g., as shown in FIGS. 1-2), the CMT exercise application 320 may determine if the user's responses correspond to the cues (e.g., by touching, moving, gesturing, or speaking based on the cues and/or within a time limit from a presented cue). The first device may generate a score based on the user's responses, the scoring indicating whether the user's responses met performance thresholds (e.g., the user's responses were the proper responses provided within threshold amounts of time). When the score exceeds a score threshold, such may indicate that the user completed the CMT exercise properly, and the next CMT exercise in the sequence of exercises may commence, repeating the interaction and evaluation processes. When the user's score is too low (e.g., the user did not respond to the cues and/or did not respond quickly enough), such may indicate that the user struggled to complete the CMT exercise properly. As a result, the first device may revise the sequence of CMT exercises by generating a different CMT exercise sequence for presentation.

In one or more embodiments, the CMT exercises may represent varying degrees of difficulty for the user to complete. For example, some CMT exercises may have longer sequences than others and therefore may be more difficult to complete. Some CMT exercises may require shorter response times to visual and audible cues than other CMT exercises. A more difficult CMT exercise may include visual disruptors that hide a character's and player's rhythmic sequences, pushing the player to use more of their acquired rhythmic skills. A sequence of CMT exercises may be organized in a manner in which the CMT exercises increase in difficulty, allowing the user 302 to begin with an easier CMT exercise, and progress to more difficult CMT exercises. The CMT exercises may include an introduction (e.g., contextualizing the game at its launch), instructions regarding how the game works (e.g., a user manual), an image and text sequence to describe a particular CMT exercise, rhythmic sequences, visual and auditory cues, audio and visual feedback, use of special effects, description of graphic assets, animation, a presentation of an "end" screen and user score, and the like. One or more CMT exercises may be part of a larger storyline so that completion of the CMT exercise tasks (e.g., user responses to the cues) allows for progression of the storyline.

In one or more embodiments, the CMT exercises may include multiple tasks for which the user 302 is cued. One task may be to "follow" a leader by tapping or otherwise touching a device (e.g., a touchscreen), such as by swiping. The tapping could be anywhere on a device, or may require a specific portion of the screen (e.g., left side vs. right side, etc.). Another task may be to clap hands according to a beat/rhythm. Another task may be to shake or otherwise move a device (e.g., according to a beat/rhythm). Another task may be to sing or provide other verbal responses according to a beat/rhythm. Another task may be to tap or otherwise touch a device in accordance with a beat/rhythm. Another task may include a motion (e.g., punching, waving, etc.) in accordance with a beat/rhythm. Another task may include a user selection of words or other objects (e.g., based on tapping, touching, etc.). User motion and gestures may be detected by the device cameras 328 (e.g., image data of the user may be analyzed to determine whether a movement was executed within a limited time period). Device motion may be detected by the device motion sensors 332 to determine whether a user moved a device within a limited time period. Audio responses (e.g., singing, talking) of a user may be detected by the microphones 330 and analyzed to determine that an audio response in general, or specific (e.g., using audio processing and natural language processing to identify keywords), was communicated within a limited time period. Device touching may be measured by the pressure sensors 326 (e.g., haptic sensors) that detect contact pressure (e.g., with a touchscreen), and may be compared to a time threshold. The time periods/thresholds used to measure whether a user's interaction occurred quickly enough to satisfy rules of a CMT exercise may be considered performance thresholds. The performance thresholds may represent amounts of time before or after a beat and during which the user 302 is required to respond according to a cue (e.g., a beat of a song, a graphic displayed, etc.). The performance thresholds also may include the length of a user action (e.g., how long the user 302 held a note when singing) or the percentage of task completion (e.g., a percentage of a song that the user 302 actually sings in comparison to an entire song).

In one or more embodiments, scoring player's performance SP may be based on rhythmic synchronization through multiple modalities of interaction (sometimes combined). Player's responses are captured through accelerometers, microphones, cameras, and pressure sensitive screens. By assessing the audio-motor synchronization of the child with the rhythmic instruction, a device may define (i) a time T which corresponds to the exact moment when the player's input is expected (whatever the interaction mode); (ii) tolerance thresholds as in a Likert scale: tPerfect<tGood<tCorrect. The different intervals allow the device to assess the quality of the user's response with four levels of acceptance. An input may be considered accepted when it is in the interval [t−tCorrect; T+tCorrect] and refused otherwise. An input of better quality, either in the interval [T−tGood; T+tGood] or in the interval [T−tPerfect; T+tPerfect], may result in a different visual and audio feedback to the child. In one version, a simplified score calculation may account for the ratio of accepted user inputs to total inputs. When a user's score exceeds a score threshold, the user has completed the CMT exercise and may progress to another (e.g., more difficult) exercise. When the user's score is below the score threshold, the user may be presented with the same CMT exercise, or another CMT exercise of similar or less difficulty.

In one or more embodiments, the devices 304 may include a personal computer (PC), a wearable wireless device (e.g., bracelet, watch, glasses, ring, etc.), a desktop computer, a mobile computer, a laptop computer, an Ultrabook™ computer, a notebook computer, a tablet computer, a server computer, a handheld computer, a handheld device, an internet of things (IoT) device, a sensor device, a PDA device, a handheld PDA device, an on-board device, an off-board device, a hybrid device (e.g., combining cellular phone functionalities with PDA device functionalities), a consumer device, a vehicular device, a non-vehicular device, a mobile or portable device, a non-mobile or non-portable device, a mobile phone, a cellular telephone, a PCS device, a PDA device which incorporates a wireless communication device, a mobile or portable GPS device, a DVB device, a relatively small computing device, a non-desktop computer, a "carry small live large" (CSLL) device, an ultra mobile device (UMD), an ultra mobile PC (UMPC), a mobile internet device (MID), an "origami" device or computing device, a device that supports dynamically composable computing (DCC), a context-aware device, a video device, an audio device, an A/V device, a set-top-box (STB), a Blu-ray disc (BD) player, a BD recorder, a digital video disc (DVD) player, a high definition (HD) DVD player, a DVD recorder, a HD DVD recorder, a personal video recorder (PVR), a broadcast HD receiver, a video source, an audio source, a video sink, an audio sink, a stereo tuner, a broadcast radio receiver, a flat panel display, a personal media player (PMP), a digital video camera (DVC), a digital audio player, a speaker, an audio receiver, an audio amplifier, a gaming device, a data source, a data sink, a digital still camera (DSC), a media player, a smartphone, a television, a music player, or the like.

Any of the devices 304 and/or the one or more remote devices 306 may be configured to communicate with each other via one or more communications networks, which may include any one of a combination of different types of suitable communications networks such as, for example, broadcasting networks, cable networks, public networks (e.g., the Internet), private networks, wireless networks, cellular networks, or any other suitable private and/or public networks.

Figure 4:
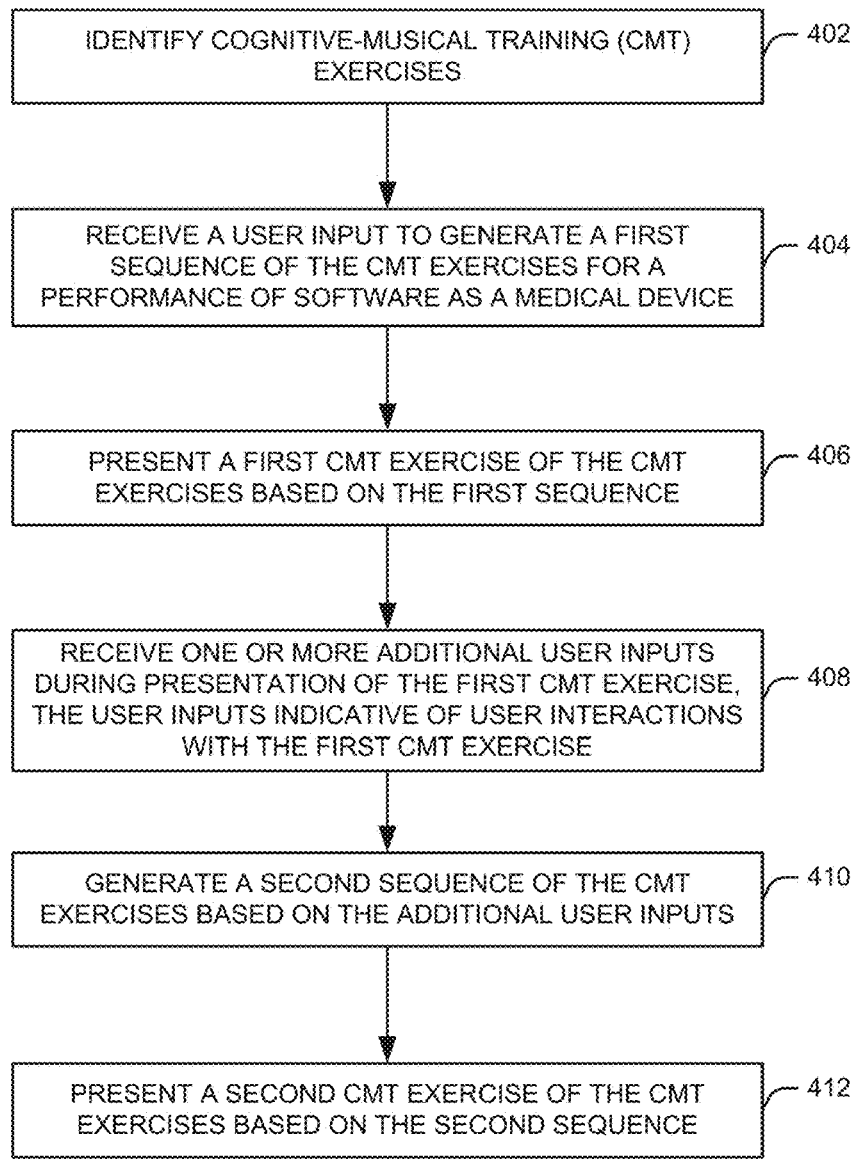
FIG. 4 illustrates a flow diagram of a process for analyzing and treating learning disorders, in accordance with one or more example embodiments of the present disclosure.

FIG. 4 illustrates a flow diagram of a process 400 for analyzing and treating learning disorders, in accordance with one or more example embodiments of the present disclosure.

At block 402, a device (e.g., the devices 304 of FIG. 3) may identify CMT exercises. The CMT exercises may be implemented as a SaMD. The CMT exercises may include a combination of interactive video and audio content. Different CMT exercises may present different challenges that test and develop cognitive abilities by providing visual and auditory cues to which a user (e.g., patient) may respond using words, gestures, touches (e.g., of screens, buttons, etc.), and the like. The CMT exercises may be maintained remotely on another device (e.g., the one or more devices 306 of FIG. 3), updated, and provided to the device, allowing the device to present the CMT exercises stored on the device without needing to connect to the other device. In this manner, the CMT exercises may be part of downloadable SaMD using a CMT application executable by the first device. In particular, the software program may be a SaMD native application that is downloadable onto the device.

At block 404, the device may receive a user input to generate a first sequence of the CMT exercises for a performance of a SaMD. The user input may represent a user initiation of the application that executes the CMT exercises, a user selection to start/begin a CMT exercise, or the like.

At block 406, the device may present a first CMT exercise of the CMT exercises based on the first sequence of CMT exercises. The device may generate a sequence of CMT exercises representing an order in which multiple CMT exercises may be presented. For example, the sequence may begin with an easier exercise (e.g., having a shorter duration, fewer cues to which the player is to respond, more time tolerance for the user to respond to the cues, etc.), and the sequence may progress with more and more difficult CMT exercises (e.g., longer duration, more cues, less time tolerance for user responses to the cues, etc.) so that the player builds upon their successes with each CMT exercise. In this manner, the device may be provided with the CMT exercises from another device, but may customize the sequence of CMT exercises locally without having to connect to the other device as the player provides the first input at block 404.

At block 408, the device may receive one or more additional user inputs during presentation of the CMT exercise. The one or more additional user inputs may represent user interactions with the CMT exercise, such as user responses to visual and audio cues that have corresponding tasks for the player. One task may be to "follow" a leader by tapping or otherwise touching a device (e.g., a touchscreen), such as by swiping. The tapping could be anywhere on a device, or may require a specific portion of the screen (e.g., left side vs. right side, etc.). Another task may be to clap hands according to a beat/rhythm. Another task may be to shake or otherwise move a device (e.g., according to a beat/rhythm). Another task may be to sing or provide other verbal responses according to a beat/rhythm. Another task may be to tap or otherwise touch a device in accordance with a beat/rhythm. Another task may include a motion (e.g., punching, waving, etc.) in accordance with a beat/rhythm. Another task may include a user selection of words or other objects (e.g., based on tapping, touching, etc.). User motion and gestures may be detected by a device camera (e.g., image data of the user may be analyzed to determine whether a movement was executed within a limited time period). Device motion may be detected by an accelerometer to determine whether a user moved a device within a limited time period. Audio responses (e.g., singing, talking) of a user may be detected by a microphone and analyzed to determine that an audio response in general, or specific (e.g., using audio processing and natural language processing to identify keywords), was communicated within a limited time period. Device touching may be measured by pressure sensors (e.g., haptic sensors) that detect contact pressure (e.g., with a touchscreen), and may be compared to a time threshold.

At block 410, the device may generate a second sequence of the CMT exercises based on the additional user inputs. For example, as the device detects the user inputs for the cued tasks of block 406, the device may compare the inputs to performance criteria (e.g., thresholds) to determine whether the inputs were received within threshold times of a cue, whether the inputs had sufficient durations with respect to threshold amounts of time, whether a number or percentage of cues were completed during presentation of the CMT exercise, and the like. The device may generate a score based on the user's responses, the scoring indicating whether the user's responses met performance thresholds (e.g., the user's responses were the proper responses provided within threshold amounts of time). When the score exceeds a score threshold, such may indicate that the user completed the CMT exercise properly, and the next CMT exercise in the sequence of exercises may commence, repeating the interaction and evaluation processes. When the user's score is too low (e.g., the user did not respond to the cues and/or did not respond quickly enough), such may indicate that the user struggled to complete the CMT exercise properly. As a result, the device may revise the sequence of CMT exercises by generating a different CMT exercise sequence for presentation. In one or more embodiments, scoring player's performance SP may be based on rhythmic synchronization through multiple modalities of interaction (sometimes combined). By assessing the audio-motor synchronization of the child with the rhythmic instruction, a device may define (i) a time T which corresponds to the exact moment when the player's input is expected (whatever the interaction mode); (ii) tolerance thresholds as in a Likert scale: tPerfect<tGood<tCorrect. The different intervals allow the device to assess the quality of the user's response with four levels of acceptance. An input may be considered accepted when it is in the interval [T−tCorrect; T+tCorrect] and refused otherwise. An input of better quality, either in the interval [T−tGood; T+tGood] or in the interval [T−tPerfect; T+tPerfect], may result in a different visual and audio feedback to the child. In one version, a simplified score calculation may account for the ratio of accepted user inputs to total inputs. When a user's score exceeds a score threshold, the user has completed the CMT exercise and may progress to another (e.g., more difficult) exercise. When the user's score is below the score threshold, the user may be presented with the same CMT exercise, or another CMT exercise of similar or less difficulty.

At block 412, the device may present a second CMT exercise (and other subsequent CMT exercises) based on the updated sequence of CMT exercises. For example, the sequence may begin with an easier exercise (e.g., having a shorter duration, fewer cues to which the player is to respond, more time tolerance for the user to respond to the cues, etc.), and the sequence may progress with more and more difficult CMT exercises (e.g., longer duration, more cues, less time tolerance for user responses to the cues, etc.) so that the player builds upon their successes with each CMT exercise.

Figure 5:
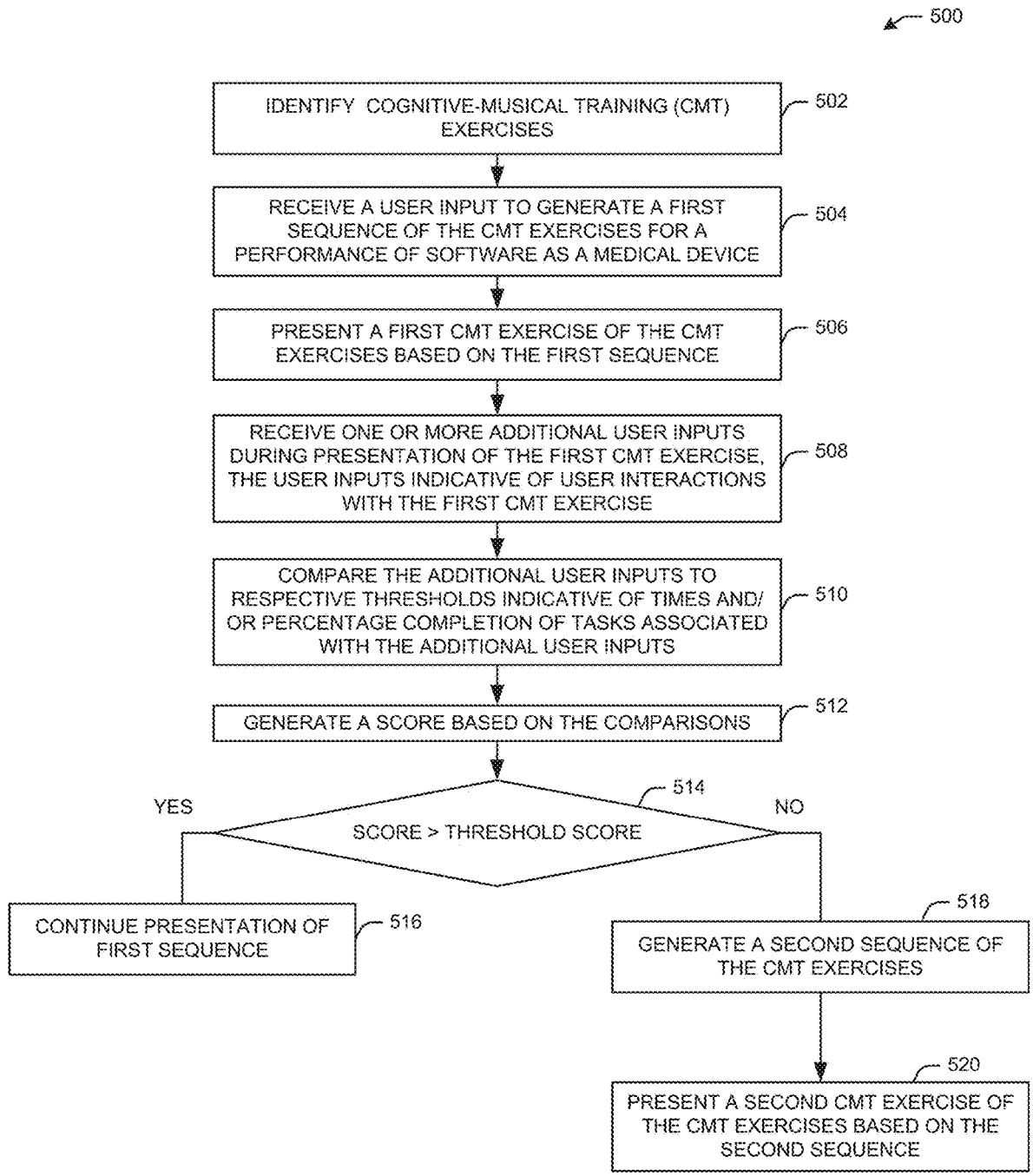
FIG. 5 illustrates a flow diagram of a process for analyzing and treating learning disorders, in accordance with one or more example embodiments of the present disclosure.

FIG. 5 illustrates a flow diagram of a process 500 for analyzing and treating learning disorders, in accordance with one or more example embodiments of the present disclosure.

At block 502, a device (e.g., the devices 304 of FIG. 3) may identify CMT exercises. The CMT exercises may be implemented as a SaMD. The CMT exercises may include a combination of interactive video and audio content. Different CMT exercises may present different challenges that test and develop cognitive abilities by providing visual and auditory cues to which a user (e.g., patient) may respond using words, gestures, touches (e.g., of screens, buttons, etc.), and the like. The CMT exercises may be maintained remotely on another device (e.g., the one or more devices 306 of FIG. 3), updated, and provided to the device, allowing the device to present the CMT exercises stored on the device without needing to connect to the other device. In this manner, the CMT exercises may be part of downloadable SaMD using a CMT computer program executable by the first device. In particular, the software program may be a SaMD native application that is downloadable onto the device.

At block 504, the device may receive a user input to generate a first sequence of the CMT exercises for a performance of a SaMD. The user input may represent a user initiation of the application that executes the CMT exercises, a user selection to start/begin a CMT exercise, or the like.

At block 506, the device may present a first CMT exercise of the CMT exercises based on the first sequence of CMT exercises. The device may generate a sequence of CMT exercises representing an order in which multiple CMT exercises may be presented. For example, the sequence may begin with an easier exercise (e.g., having a shorter duration, fewer cues to which the player is to respond, more time tolerance for the user to respond to the cues, etc.), and the sequence may progress with more and more difficult CMT exercises (e.g., longer duration, more cues, less time tolerance for user responses to the cues, etc.) so that the player builds upon their successes with each CMT exercise. In this manner, the device may be provided with the CMT exercises from another device, but may customize the sequence of CMT exercises locally without having to connect to the other device as the player provides the first input at block 504.

At block 508, the device may receive one or more additional user inputs during presentation of the CMT exercise. The one or more additional user inputs may represent user interactions with the CMT exercise, such as user responses to visual and audio cues that have corresponding tasks for the player. One task may be to "follow" a leader by tapping or otherwise touching a device (e.g., a touchscreen), such as by swiping. The tapping could be anywhere on a device, or may require a specific portion of the screen (e.g., left side vs. right side, etc.). Another task may be to clap hands according to a beat/rhythm. Another task may be to shake or otherwise move a device (e.g., according to a beat/rhythm). Another task may be to sing or provide other verbal responses according to a beat/rhythm. Another task may be to tap or otherwise touch a device in accordance with a beat/rhythm. Another task may include a motion (e.g., punching, waving, etc.) in accordance with a beat/rhythm. Another task may include a user selection of words or other objects (e.g., based on tapping, touching, etc.).

At block 510, the device may compare the additional user inputs to respective thresholds (e.g., performance criteria) indicative of times and/or percentage completion of tasks that the user was cued to perform. User motion and gestures may be detected by a device camera (e.g., image data of the user may be analyzed to determine whether a movement was executed within a limited time period). Device motion may be detected by an accelerometer to determine whether a user moved a device within a limited time period. Audio responses (e.g., singing, talking) of a user may be detected by a microphone and analyzed to determine that an audio response in general, or specific (e.g., using audio processing and natural language processing to identify keywords), was communicated within a limited time period. Device touching may be measured by pressure sensors (e.g., haptic sensors) that detect contact pressure (e.g., with a touchscreen), and may be compared to a time threshold. The time periods/thresholds used to measure whether a user's interaction occurred quickly enough to satisfy rules of a CMT exercise may be considered performance thresholds. The performance thresholds may represent amounts of time before or after a beat and during which the user is required to respond according to a cue (e.g., a beat of a song, a graphic displayed, etc.). The performance thresholds also may include the length of a user action (e.g., how long the user held a note when singing) or the percentage of task completion (e.g., a percentage of a song that the user actually sings in comparison to an entire song).

At block 512, the device may generate a user score based on the comparisons of the user inputs to the performance criteria. The device may generate a score based on the user's responses, the scoring indicating whether the user's responses met performance thresholds (e.g., the user's responses were the proper responses provided within threshold amounts of time). When the score exceeds a score threshold, such may indicate that the user completed the CMT exercise properly, and the next CMT exercise in the sequence of exercises may commence, repeating the interaction and evaluation processes. When the user's score is too low (e.g., the user did not respond to the cues and/or did not respond quickly enough), such may indicate that the user struggled to complete the CMT exercise properly.

At block 514, the device may determine whether the user's score exceeds a threshold score. When the score exceeds the threshold score (indicative of a satisfactory user performance), the process 500 may continue to block 516, where the device may continue the presentation of the CMT exercises according to the first sequence (e.g., may progress to the next CMT exercise in the sequence). When the score does not exceed the threshold score (indicative of unsatisfactory user performance), the process 500 may continue to block 518, where the device may generate a second sequence of CMT exercises. The second sequence may include a different sequential order of the CMT exercises and/or new/modified CMT exercises (e.g., as provided by the one or more remote devices 306 of FIG. 3). In particular, the second sequence may begin with the same CMT exercise, another CMT exercise of similar difficulty, or another CMT exercise of less difficulty. The CMT exercises of the second sequence may progress in difficulty.

At block 518, the device may present a second CMT exercise as part of the second sequence. Blocks 508-514 may be repeated to evaluate the user's responses to the cues in the second CMT exercise, and to determine whether the user satisfied the performance criteria, before either progressing to another CMT exercise or generating another modified sequence of CMT exercises.

Figure 6:
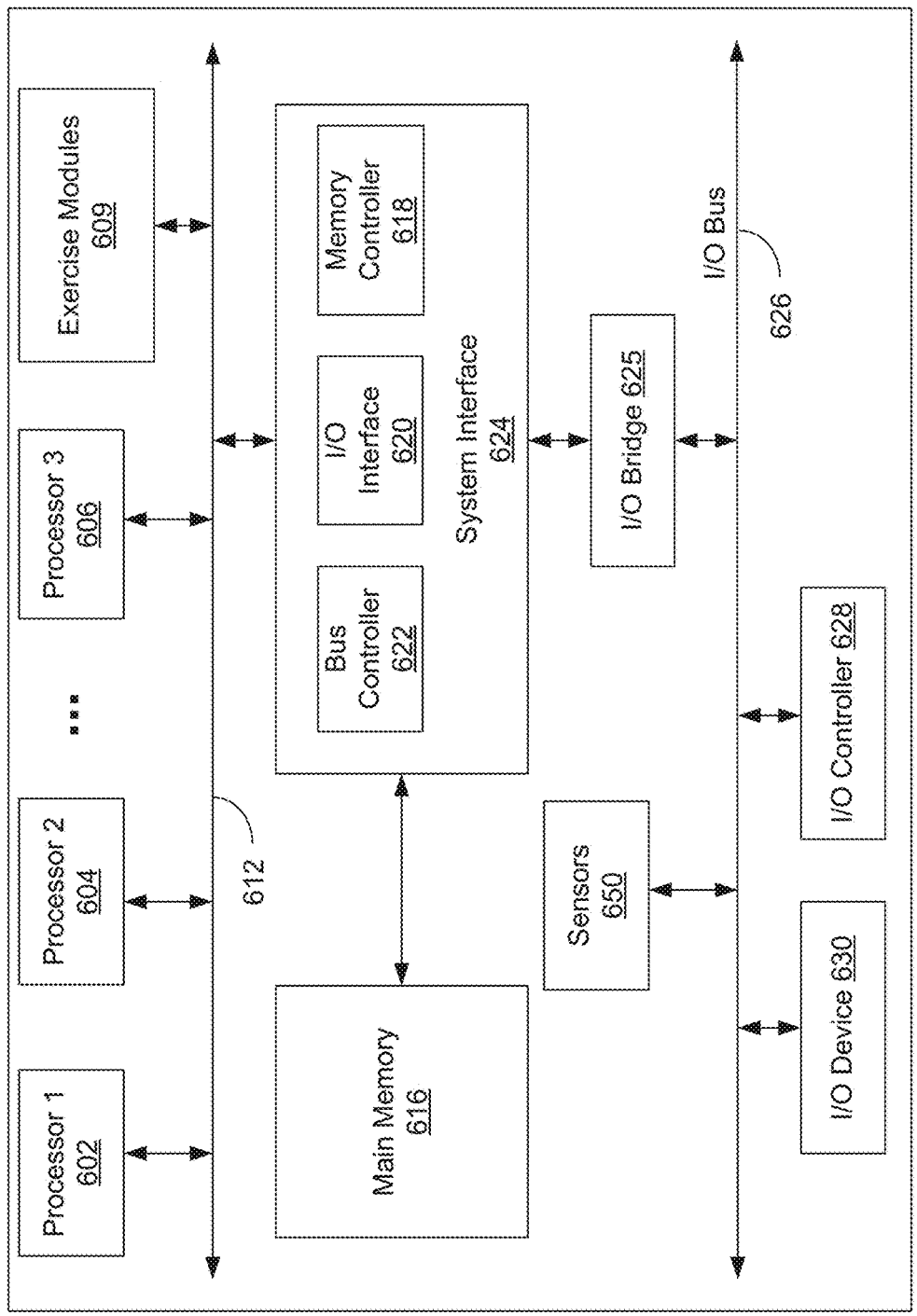
FIG. 6 is a block diagram illustrating an example of a computing device or computer system upon which any of one or more techniques (e.g., methods) may be performed, in accordance with one or more example embodiments of the present disclosure.

FIG. 6 is a block diagram illustrating an example of a computing device or computer system 600 upon which any of one or more techniques (e.g., methods) may be performed, in accordance with one or more example embodiments of the present disclosure.

For example, the computing system 600 of FIG. 6 may represent the devices 304 and/or the one or more devices 306 of FIG. 3, and therefore may facilitate the generation of CMT exercises, the generation of CMT exercise sequences, the presentation of CMT exercise sequences, the detection of user inputs, and the evaluation of user performance based on the user inputs, allowing the CMT exercises to perform as a SaMD. The computer system (system) includes one or more processors 602-606 and one or more exercise modules 609 (e.g. representing the exercise application 320 and/or the CMT exercise modules 310 of FIG. 3). Processors 602-606 may include one or more internal levels of cache (not shown) and a bus controller (e.g., bus controller 622) or bus interface (e.g., I/O interface 620) unit to direct interaction with the processor bus 612.

Processor bus 612, also known as the host bus or the front side bus, may be used to couple the processors 602-606 with the system interface 624. System interface 624 may be connected to the processor bus 612 to interface other components of the system 600 with the processor bus 612. For example, system interface 624 may include a memory controller 618 for interfacing a main memory 616 with the processor bus 612. The main memory 616 typically includes one or more memory cards and a control circuit (not shown). System interface 624 may also include an input/output (I/O) interface 620 to interface one or more I/O bridges 625 or I/O devices 630 with the processor bus 612. One or more I/O controllers and/or I/O devices may be connected with the I/O bus 626, such as I/O controller 628 and I/O device 630, as illustrated.

I/O device 630 may also include an input device (not shown), such as an alphanumeric input device, including alphanumeric and other keys for communicating information and/or command selections to the processors 602-606. Another type of user input device includes cursor control, such as a mouse, a trackball, or cursor direction keys for communicating direction information and command selections to the processors 602-606 and for controlling cursor movement on the display device.

System 600 may include a dynamic storage device, referred to as main memory 616, or a random access memory (RAM) or other computer-readable devices coupled to the processor bus 612 for storing information and instructions to be executed by the processors 602-606. Main memory 616 also may be used for storing temporary variables or other intermediate information during execution of instructions by the processors 602-606. System 600 may include read-only memory (ROM) and/or other static storage device coupled to the processor bus 612 for storing static information and instructions for the processors 602-606. The system outlined in FIG. 6 is but one possible example of a computer system that may employ or be configured in accordance with aspects of the present disclosure.

According to one embodiment, the above techniques may be performed by computer system 600 in response to processor 604 executing one or more sequences of one or more instructions contained in main memory 616. These instructions may be read into main memory 616 from another machine-readable medium, such as a storage device. In alternative embodiments, circuitry may be used in place of or in combination with the software instructions. Thus, embodiments of the present disclosure may include both hardware and software components.

The computer system 600 may include sensors 650, which may include a combination of pressure sensors (e.g., the pressure sensors 326 of FIG. 3), cameras (e.g., the cameras 328 of FIG. 3), microphones (e.g., the microphones 330 of FIG. 3), and device motion sensors (e.g., the device motion sensors 332 of FIG. 3).

Various embodiments may be implemented fully or partially in software and/or firmware. This software and/or firmware may take the form of instructions contained in or on a non-transitory computer-readable storage medium. Those instructions may then be read and executed by one or more processors to enable the performance of the operations described herein. The instructions may be in any suitable form, such as, but not limited to, source code, compiled code, interpreted code, executable code, static code, dynamic code, and the like. Such a computer-readable medium may include any tangible non-transitory medium for storing information in a form readable by one or more computers, such as but not limited to read-only memory (ROM); random access memory (RAM); magnetic disk storage media; optical storage media; a flash memory, etc.

A machine-readable medium includes any mechanism for storing or transmitting information in a form (e.g., software, processing application) readable by a machine (e.g., a computer). Such media may take the form of, but is not limited to, non-volatile media and volatile media and may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, solid state devices (SSDs), and the like. The one or more memory devices (not shown) may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in main memory 616, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

Embodiments of the present disclosure include various steps, which are described in this specification. The steps may be performed by hardware components or may be embodied in machine-executable instructions, which may be used to cause a general-purpose or special-purpose processor programmed with the instructions to perform the steps. Alternatively, the steps may be performed by a combination of hardware, software, and/or firmware.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations together with all equivalents thereof.

The operations and processes described and shown above may be carried out or performed in any suitable order as desired in various implementations. Additionally, in certain implementations, at least a portion of the operations may be carried out in parallel. Furthermore, in certain implementations, less than or more than the operations described may be performed.

The word "exemplary" is used herein to mean "serving as an example, instance, or illustration." Any embodiment described herein as "exemplary" is not necessarily to be construed as preferred or advantageous over other embodiments.

As used herein, unless otherwise specified, the use of the ordinal adjectives "first," "second," "third," etc., to describe a common object, merely indicates that different instances of like objects are being referred to and are not intended to imply that the objects so described must be in a given sequence, either temporally, spatially, in ranking, or any other manner.

It is understood that the above descriptions are for purposes of illustration and are not meant to be limiting.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

What is claimed is:

1. A method for medical analysis of learning disorders of a patient, the method comprising:
   identifying, by at least one processor of a device, application-based cognitive musical training (CMT) exercises associated with performance of software, the application-based CMT exercises comprising video and audio;
   receiving, by the at least one processor, a first user input to generate a first sequence of the application-based CMT exercises;
   presenting, by the at least one processor, a first application-based CMT exercise of the application-based CMT exercises based on the first sequence;
   receiving, by the at least one processor, during the presentation of the first application-based CMT exercise, a second user input of a first modality, the second user input indicative of a first user interaction with the first application-based CMT exercise;
   determining, by the at least one processor, that the second user input is within a first performance threshold associated with the first modality;
   receiving, by the at least one processor, during the presentation of the first application-based CMT exercise, a third user input of a second modality different than the first modality, the third user input indicative of a second user interaction with the first application-based CMT exercise;
   determining, by the at least one processor, that the third user input is within a second performance threshold associated with the second modality, the second performance threshold different than the first performance threshold;
   determining, by the at least one processor, a number of first user inputs of the first modality received during the presentation of the first application-based CMT exercise that are within the first performance threshold, the number of first user inputs within the first performance threshold comprising the second user input;
   determining, by the at least one processor, a number of second user inputs of the second modality received during the presentation of the first application-based CMT exercise that are within the second performance threshold, the number of second user inputs within the second performance threshold comprising the third user input;
   determining, by the at least one processor, that the number of first user inputs within the first performance threshold and the number of second user inputs within the second performance threshold are below a third performance threshold;
   generating, by the at least one processor, based on the determination that the number of first user inputs within the first performance threshold and the number of second user inputs within the second performance threshold are below the third performance threshold, a second sequence of the application-based CMT exercises, the first sequence different than the second sequence; and
   presenting, by the at least one processor, a second application-based CMT exercise of the application-based CMT exercises based on the second sequence.

2. The method of claim 1, wherein the first modality is a contact pressure with the device indicative of a user tapping the device, and wherein the first performance threshold is a time threshold, the method further comprising:
   determining a first time associated with a rhythm of the audio;
   determining a second time associated with the user tapping; and
   determining that the second time occurs within the time threshold of the first time, wherein determining that the second user input is within the first performance threshold is based on the determination that the second time occurs within the time threshold of the first time.

3. The method of claim 1, wherein the first modality is a sound indicative of a user clapping, and wherein the first performance threshold is a time threshold, the method further comprising:
determining a first time associated with a rhythm of the audio;
determining a second time associated with the user clapping; and
determining that the second time occurs within the time threshold of the first time,
wherein determining that the second user input is within the first performance threshold is based on the determination that the second time occurs within the time threshold of the first time.

4. The method of claim 1, wherein the first modality is device motion data indicative of a user shaking the device, and wherein the first performance threshold is a time threshold, the method further comprising:
determining a first time associated with a rhythm of the audio;
determining a second time associated with the user shaking; and
determining that the second time occurs within the time threshold of the first time,
wherein determining that the second user input is within the first performance threshold is based on the determination that the second time occurs within the time threshold of the first time.

5. The method of claim 1, wherein the first modality is a sound indicative of a user singing, and wherein the first performance threshold is a time threshold, the method further comprising:
determining a first time associated with a rhythm of the audio;
determining a second time associated with the user singing; and
determining that the second time occurs within the time threshold of the first time,
wherein determining that the second user input is within the first performance threshold is based on the determination that the second time occurs within the time threshold of the first time.

6. The method of claim 1, wherein the first modality is video data indicative of a user motion captured by a camera of the device, and wherein the first performance threshold is a time threshold, the method further comprising:
determining a first time associated with a rhythm of the audio;
determining a second time associated with the user motion; and
determining that the second time occurs within the time threshold of the first time,
wherein determining that the second user input is within the first performance threshold is based on the determination that the second time occurs within the time threshold of the first time.

7. The method of claim 1, further comprising:
after the presentation of the first application-based CMT exercise, generating, based on the second user input, a score indicative of the number of first user inputs within the first performance threshold and of the number of second user inputs within the second performance threshold, wherein generating the second sequence is further based on the score.

8. The method of claim 1, further comprising:
receiving, during the presentation of the first application-based CMT exercise, a fourth user input indicative of a third user interaction with the first application-based CMT exercise,
wherein generating the second sequence is further based on a comparison of the fourth user input to a fourth performance threshold different than the first performance threshold and the second performance threshold.

9. The method of claim 8, wherein the third user input and the fourth user input comprise at least two of an auditory input, a visual input, a sensory input, or a device motion input.

10. A device comprising memory coupled to at least one processor, the at least one processor configured to:
identify application-based cognitive musical training (CMT) exercises associated with performance of software, the application-based CMT exercises comprising video and audio;
receive a first user input to generate a first sequence of the application-based CMT exercises;
present a first application-based CMT exercise of the application-based CMT exercises based on the first sequence;
receive, during the presentation of the first application-based CMT exercise, a second user input of a first modality, the second user input indicative of a first user interaction with the first application-based CMT exercise;
determine that the second user input is within a first performance threshold associated with the first modality;
receive, during the presentation of the first application-based CMT exercise, a third user input of a second modality different than the first modality, the third user input indicative of a second user interaction with the first application-based CMT exercise;
determine that the third user input is within a second performance threshold associated with the second modality, the second performance threshold different than the first performance threshold;
determine a number of first user inputs of the first modality received during the presentation of the first application-based CMT exercise that are within the first performance threshold, the number of first user inputs within the first performance threshold comprising the second user input;
determine a number of second user inputs of the second modality received during the presentation of the first application-based CMT exercise that are within the second performance threshold, the number of second user inputs within the second performance threshold comprising the third user input;
determine that the number of first user inputs within the first performance threshold and the number of second user inputs within the second performance threshold are below a third performance threshold;
generate, based on the determination that the number of first user inputs within the first performance threshold and the number of second inputs within the second performance threshold are below the third performance threshold, a second sequence of the application-based CMT exercises, the first sequence different than the second sequence; and present, a second application-based CMT exercise of the application-based CMT exercises based on the second sequence.

11. The device of claim 10, wherein the first modality is device motion data indicative of a user shaking the device, wherein the first performance threshold is a time threshold, and wherein the at least one processor is further configured to:
  determine a first time associated with a rhythm of the audio;
  determine a second time associated with the user shaking; and
  determine that the second time occurs within the time threshold of the first time,
  wherein to determine that the second user input is within the first performance threshold is based on the determination that the second time occurs within the time threshold of the first time.

12. The device of claim 10, wherein the first modality is A sound indicative of a user singing, wherein the first performance threshold is a time threshold, and wherein the at least one processor is further configured to:
  determine a first time associated with a rhythm of the audio;
  determine a second time associated with the user singing; and
  determine that the second time occurs within the time threshold of the first time,
  wherein to determine that the second user input is within the first performance threshold is based on the determination that the second time occurs within the time threshold of the first time.

13. The device of claim 10, wherein the first modality is video data indicative of a user motion captured by a camera of the device, wherein the first performance threshold is a time threshold, and wherein the at least one processor is further configured to:
  determine a first time associated with a rhythm of the audio;
  determine a second time associated with the user motion; and
  determine that the second time occurs within the time threshold of the first time,
  wherein to determine that the second user input is within the first performance threshold is based on the determination that the second time occurs within the time threshold of the first time.

14. A system comprising:
  an input device; and
  memory coupled to at least one processor, the at least one processor configured to:
    identify application-based cognitive musical training (CMT) exercises associated with performance of software, the application-based CMT exercises comprising video and audio;
    receive a first user input to generate a first sequence of the application-based CMT exercises;
    present a first application-based CMT exercise of the application-based CMT exercises based on the first sequence;
    receive, using the input device, during the presentation of the first application-based CMT exercise, a second user input of a first modality, the second user input indicative of a first user interaction with the first application-based CMT exercise;
    determine that the second user input is within a first performance threshold associated with the first modality;
    receive, during the presentation of the first application-based CMT exercise, a third user input of a second modality different than the first modality, the third user input indicative of a second user interaction with the first application-based CMT exercise;
    determine that the third user input is within a second performance threshold associated with the second modality, the second performance threshold different than the first performance threshold;
    determine a number of first user inputs of the first modality received during the presentation of the first application-based CMT exercise that are within the first performance threshold, the number of first user inputs within the first performance threshold comprising the second user input;
    determine a number of second user inputs of the second modality received during the presentation of the first application-based CMT exercise that are within the second performance threshold, the number of second user inputs within the second performance threshold comprising the third user input;
    determine that the number of first user inputs within the first performance threshold and the number of second user inputs within the second performance threshold are below a third performance threshold;
    generate, based on a the determination that the number of first user inputs within the first performance threshold and the number of second user inputs within the second performance threshold are below the third performance threshold, a second sequence of the application-based CMT exercises, the first sequence different than the second sequence; and
    present, a second application-based CMT exercise of the application-based CMT exercises based on the second sequence.

15. The system of claim 14, wherein the first modality is a contact pressure with the input device indicative of a user tapping the input device, wherein the first performance threshold is a time threshold, and wherein the at least one processor is further configured to:
  determine a first time associated with a rhythm of the audio;
  determine a second time associated with the user tapping; and
  determine that the second time occurs within the time threshold of the first time,
  wherein to determine that the second user input is within the first performance threshold is based on the determination that the second time occurs within the time threshold of the first time.

16. The system of claim 14, wherein the input device is a microphone, an accelerometer, a camera, or a haptic sensor.

17. The method of claim 1, further comprising:
  determining that the second user input is outside of a fourth performance threshold; and
  determining a third number of user inputs received during the presentation of the first application-based CMT exercise that are within the fourth performance threshold, the third number of user inputs within the fourth performance threshold excluding the second user input,
  wherein generating the second sequence is further based on the third number of user inputs.

18. The method of claim 1, further comprising:
   determining that the second user input is within a fourth performance threshold; and
   determining a third number of user inputs received during the presentation of the first application-based CMT exercise that are within the fourth performance threshold, the third number of user inputs within the fourth performance threshold comprising the second user input,
   wherein generating the second sequence is further based on the third number of user inputs.

19. The device of claim 10, wherein the at least one processor is further configured to:
   determine that the second user input is outside of a fourth performance threshold; and
   determine a third number of user inputs received during the presentation of the first application-based CMT exercise that are within the fourth performance threshold, the third number of user inputs within the fourth performance threshold excluding the second user input,
   wherein to generate the second sequence is further based on the third number of user inputs.

20. The device of claim 10, wherein the at least one processor is further configured to:
   determine that the second user input is within a fourth performance threshold; and
   determine a third number of user inputs received during the presentation of the first application-based CMT exercise that are within the fourth performance threshold, the third number of user inputs within the fourth performance threshold comprising the second user input,
   wherein to generate the second sequence is further based on the third number of user inputs.

21. The device of claim 10, wherein the first modality is a sound indicative of a user clapping, wherein the first performance threshold is a time threshold, and wherein the at least one processor is further configured to:
   determine a first time associated with a rhythm of the audio;
   determine a second time associated with the user clapping; and
   determine that the second time occurs within the time threshold of the first time,
   wherein to determine that the second user input is within the first performance threshold is based on the determination that the second time occurs within the time threshold of the first time.

22. The device of claim 10, wherein the first modality is a contact pressure with the device indicative of a user tapping the device, wherein the first performance threshold is a time threshold, and wherein the at least one processor is further configured to:
   determine a first time associated with a rhythm of the audio;
   determine a second time associated with the user tapping; and
   determine that the second time occurs within the time threshold of the first time,
   wherein to determine that the second user input is within the first performance threshold is based on the determination that the second time occurs within the time threshold of the first time.

23. The system of claim 14, wherein the first modality is a sound indicative of a user clapping, wherein the first performance threshold is a time threshold, and wherein the at least one processor is further configured to:
   determine a first time associated with a rhythm of the audio;
   determine a second time associated with the user clapping; and
   determine that the second time occurs within the time threshold of the first time,
   wherein to determine that the second user input is within the first performance threshold is based on the determination that the second time occurs within the time threshold of the first time.

24. The system of claim 14, wherein the first modality is device motion data indicative of a user shaking the system, wherein the first performance threshold is a time threshold, and wherein the at least one processor is further configured to:
   determine a first time associated with a rhythm of the audio;
   determine a second time associated with the user shaking; and
   determine that the second time occurs within the time threshold of the first time,
   wherein to determine that the second user input is within the first performance threshold is based on the determination that the second time occurs within the time threshold of the first time.

25. The system of claim 14, wherein the at least one processor is further configured to:
   determine that the second user input is outside of a fourth performance threshold; and
   determine a third number of user inputs received during the presentation of the first application-based CMT exercise that are within the fourth performance threshold, the third number of user inputs within the fourth performance threshold excluding the second user input,
   wherein to generate the second sequence is further based on the third number of user inputs.

26. The system of claim 14, wherein the at least one processor is further configured to:
   determine that the second user input is within a fourth performance threshold; and
   determine a third number of user inputs received during the presentation of the first application-based CMT exercise that are within the fourth performance threshold, the third number of user inputs within the fourth performance threshold comprising the second user input,
   wherein to generate the second sequence is further based on the third number of user inputs.

27. A non-transitory computer-readable storage medium comprising instructions to cause at least one processor of a device, upon execution of the instructions by the at least one processor, to:
   identify application-based cognitive musical training (CMT) exercises associated with performance of software, the application-based CMT exercises comprising video and audio;
   receive a first user input to generate a first sequence of the application-based CMT exercises;
   present a first application-based CMT exercise of the application-based CMT exercises based on the first sequence;
   receive, using an input device, during the presentation of the first application-based CMT exercise, a second user input of a first modality, the second user input indicative of a user interaction with the first application-based CMT exercise;

determine that the second user input is within a first performance threshold associated with the first modality;

receive, during the presentation of the first application-based CMT exercise, a third user input of a second modality different than the first modality, the third user input indicative of a second user interaction with the first application-based CMT exercise;

determine that the third user input is within a second performance threshold associated with the second modality, the second performance threshold different than the first performance threshold;

determine a number of first user inputs of the first modality received during the presentation of the first application-based CMT exercise that are within the first performance threshold, the number of first user inputs within the first performance threshold comprising the second user input;

determine a number of second user inputs of the second modality received during the presentation of the first application-based CMT exercise that are within the second performance threshold, the number of second user inputs within the second performance threshold comprising the third user input;

determine that the number of first user inputs within the first performance threshold and the number of second user inputs within the second performance threshold are below a third performance threshold;

generate, based on a the determination that the number of first user inputs within the first performance threshold and the number of second user inputs below the second performance threshold are below the third performance threshold, a second sequence of the application-based CMT exercises, the first sequence different than the second sequence; and present, a second application-based CMT exercise of the application-based CMT exercises based on the second sequence.

28. The non-transitory computer-readable storage medium of claim 27, wherein the first modality is a contact pressure with the input device indicative of a user tapping the input device, wherein the first performance threshold is a time threshold, and wherein execution of the instructions further causes the at least one processor to:

determine a first time associated with a rhythm of the audio;

determine a second time associated with the user tapping; and determine that the second time occurs within the time threshold of the first time, wherein to determine that the second user input is within the first performance threshold is based on the determination that the second time occurs within the time threshold of the first time.

29. The non-transitory computer-readable storage medium of claim 27, wherein the first modality is a sound indicative of a user clapping, wherein the first performance threshold is a time threshold, and wherein execution of the instructions further causes the at least one processor to:

determine a first time associated with a rhythm of the audio;

determine a second time associated with the user clapping; and determine that the second time occurs within the time threshold of the first time, wherein to determine that the second user input is within the first performance threshold is based on the determination that the second time occurs within the time threshold of the first time.

30. The non-transitory computer-readable storage medium of claim 27, wherein the first modality is device motion data indicative of a user shaking the device, wherein the first performance threshold is a time threshold, and wherein execution of the instructions further causes the at least one processor to:

determine a first time associated with a rhythm of the audio;

determine a second time associated with the user shaking; and determine that the second time occurs within the time threshold of the first time, wherein to determine that the second user input is within the first performance threshold is based on the determination that the second time occurs within the time threshold of the first time.

* * * * *